(12) United States Patent
Cloutier et al.

(10) Patent No.: US 12,245,950 B2
(45) Date of Patent: Mar. 11, 2025

(54) INTERBODY CAGE DEVICE AND METHOD FOR PERFORMING SPINAL SURGICAL PROCEDURES

(71) Applicant: NovApproach Spine, LLC, Alachua, FL (US)

(72) Inventors: Raymond Cloutier, Alachua, FL (US); Michael MacMillan, St. Petersburg, FL (US)

( * ) Notice: Subject to any disclaimer, the term of this patent is extended or adjusted under 35 U.S.C. 154(b) by 0 days.

(21) Appl. No.: 18/143,594

(22) Filed: May 4, 2023

(65) Prior Publication Data
US 2023/0355405 A1      Nov. 9, 2023

Related U.S. Application Data

(60) Provisional application No. 63/338,117, filed on May 4, 2022.

(51) Int. Cl.
| | |
|---|---|
| *A61F 2/44* | (2006.01) |
| *A61F 2/46* | (2006.01) |
| *A61F 2/30* | (2006.01) |

(52) U.S. Cl.
CPC .......... *A61F 2/4455* (2013.01); *A61F 2/4611* (2013.01); *A61F 2002/30242* (2013.01); *A61F 2002/443* (2013.01); *A61F 2002/4485* (2013.01)

(58) Field of Classification Search
CPC .... A61F 2/4455; A61F 2/4611; A61F 2/4422; A61F 2/44; A61F 2002/30242; A61F 2002/443; A61F 2002/4485; A61F 2002/4415

USPC .......................................... 623/17.11–17.16
See application file for complete search history.

(56) References Cited

U.S. PATENT DOCUMENTS

| | | | | |
|---|---|---|---|---|
| 5,554,194 A | * | 9/1996 | Sanders | A61F 2/30721 403/65 |
| 5,755,797 A | * | 5/1998 | Baumgartner | A61F 2/441 623/17.16 |
| 5,756,127 A | * | 5/1998 | Grisoni | A61K 9/0024 424/9.4 |
| 6,183,768 B1 | * | 2/2001 | Harle | A61K 9/0024 424/423 |
| 7,806,933 B2 | * | 10/2010 | Sears | A61F 2/4425 623/17.11 |
| 8,021,429 B2 | * | 9/2011 | Viker | A61F 2/4611 623/17.11 |
| 8,632,591 B2 | * | 1/2014 | Vila | A61F 2/4465 623/17.11 |
| 9,101,475 B2 | * | 8/2015 | Wei | A61F 2/30 |
| 9,289,240 B2 | * | 3/2016 | Messerli | A61F 2/441 |

(Continued)

*Primary Examiner* — Jessica Weiss
(74) *Attorney, Agent, or Firm* — Maxwell L. Minch; Maxwell L Minch Esq. PA (57) ABSTRACT

The present invention provides for improved interbody cage devices using surgical methods for delivering such cage into the disc space. The present invention has at least one advantage of providing practical and advantageous methods for accessing the spinal disc space to insert and deploy interbody cage devices in various manners that overcome the disadvantages of posterior, trans-sacro-iliac, anterior, oblique and lateral approaches thereto and minimize surgical trauma to the patient. Thus, the present invention provides for the unmet need for improved interbody cage devices which may be inserted to a disc space for patients exhibiting a wide range of anatomies.

21 Claims, 9 Drawing Sheets

(56) References Cited

U.S. PATENT DOCUMENTS

| | | | | |
|---|---|---|---|---|
| 9,375,320 | B2* | 6/2016 | Walker | A61F 2/4611 |
| 9,877,843 | B2* | 1/2018 | Vickers | A61F 2/4455 |
| 10,500,062 | B2* | 12/2019 | Marchek | A61F 2/447 |
| 2006/0247781 | A1* | 11/2006 | Francis | A61F 2/442 |
| | | | | 606/78 |
| 2006/0265077 | A1* | 11/2006 | Zwirkoski | A61F 2/442 |
| | | | | 623/17.14 |
| 2008/0009792 | A1* | 1/2008 | Henniges | A61B 17/8805 |
| | | | | 604/510 |
| 2009/0005871 | A1* | 1/2009 | White | A61F 2/30721 |
| | | | | 606/232 |
| 2009/0240335 | A1* | 9/2009 | Arcenio | A61B 17/7094 |
| | | | | 623/17.11 |
| 2009/0292362 | A1* | 11/2009 | Allard | A61F 2/4425 |
| | | | | 623/17.14 |
| 2012/0310355 | A1* | 12/2012 | Dutoit | A61B 17/7094 |
| | | | | 623/17.16 |
| 2013/0173004 | A1* | 7/2013 | Greenhalgh | A61F 2/4455 |
| | | | | 623/17.16 |
| 2016/0120661 | A1* | 5/2016 | Schell | A61B 17/8605 |
| | | | | 623/17.11 |

* cited by examiner

INTERBODY CAGE DEVICE AND METHOD FOR PERFORMING SPINAL SURGICAL PROCEDURES

CROSS-REFERENCE TO RELATED APPLICATIONS

This application claims the benefit of U.S. Provisional Application No. 63/338,117, having a filing date of May 4, 2022, the disclosure of which is hereby incorporated by reference in its entirety and all commonly owned.

FIELD OF THE INVENTION

The present disclosure generally relates to methods for performing spinal surgical procedures in a human. More particularly, the disclosure generally relates to methods for performing spinal surgical procedures by accessing a spinal column.

BACKGROUND OF THE INVENTION

Lower back pain is quite common amongst the regular population. While most lower back pain is alleviated with weight loss, exercise, medication, physical therapy, or chiropractic care, there still remains several persons who will undergo some sort of surgical intervention to alleviate their lower back pain Surgical interventions include laminectomy, which removes herniated disc material causing the low back pain, and interbody fusion which involves the insertion of a cage to maintain disc height, help protect the nerve root, and restores weight-bearing to anterior structures. However, depending on the approach the insertion of interbody cages often requires multiple insertions.

Minimal invasive surgery (MIS) has several benefits over more traditional surgical techniques. Benefits include a lower rate of morbidity, reduced pain, reduced scarring, reduced blood loss and reduced recovery time and costs. In minimal invasive spine surgery, small incisions, typically about 0.5 to about 4.0 centimeters in length, are made in, for example a patient's back.

A further extension of minimally invasive surgery that is being developed currently involves using instruments that are operated and controlled by robots to access internal cavities, bones and organs within subjects. Robotic spine surgery uses conventional surgical access locations and approaches, for example, the central region of a patient's back (i.e. 'posterior approach'). Robotic spine surgery provides benefits in accuracy and reproducibility for placing spinal implants. Robotic spine surgery is often used to position a surgical instrument in accordance with a virtual image of a patient's anatomy that is generated by an MRI or CT scan. In addition to the improved accuracy and reproducibility that a robot provides, the robot has the potential to reduce the size of the surgical incision in order to provide the patient a less invasive surgery, and thus reduced trauma to the subject.

A further extension of minimally invasive surgery that is being developed currently involves using augmented reality software to aid in the guidance of instruments to access internal cavities, bones and organs within subjects. Augmented reality surgery uses conventional surgical access locations and approaches, for example, the central region of a patient's back (i.e. 'posterior approach'). Augmented reality spine surgery provides benefits in accuracy and reproducibility for placing spinal implants. Augmented reality surgery is often used to position a surgical instrument in accordance with a virtual image of a patient's anatomy that is generated by an MRI or CT scan. In addition to the improved accuracy and reproducibility that augmented reality provides, augmented reality surgery has the potential to reduce the size of the surgical incision in order to provide the patient a less invasive surgery, and thus reduced trauma to the subject.

Cage insertion is typically limited to posterior and anterior approaches because of limitations with other approaches, such as ala as the pathway to the L5 vertebrae and L5/S1 disc space without violating the sacro-iliac joint. Particularly the ala as the pathway to the L5 vertebrae and L5/S1 disc space is limited and only small tools can be passed through that pathway. Thus, there remains an unmet need in providing an interbody cage which can be inserted to the L5/S1 disc space without violating the sacro-iliac joint.

SUMMARY OF INVENTION

The present invention provides for an improved interbody cage which may be inserted using a pathway to the L5/S1 or another disc space without violating the sacro-iliac joint or other important anatomic structures. Another aspect of the present invention is to provide practical and advantageous methods for accessing the spinal vertebrae to insert interbody cages in various manners that overcome the disadvantages of posterior, trans-sacro-iliac, anterior, oblique and lateral approaches thereto and minimize surgical trauma to the patient. Yet, another aspect of the present invention provides for mechanical, augmented reality and robot methods and pathways to optimize spinal fusion and implant surgeries.

BRIEF DESCRIPTION OF THE DRAWINGS

Examples illustrative of embodiments of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings. The figures (Figs.) are listed below.

FIGS. 5A-5F illustrates embodiments of a beaded interbody cage device using one or more geometric structures being capable of being delivered through surgical cannulas used in spinal surgeries through the ala or another anatomic region as the pathway to the L5/S1 disc space or any other disc space along the spine. FIG. 5A illustrates the 500 interbody implant with the selected geometric shape being a truncated prolate sphere, and further illustrating the separate spherical structures prior to interconnection, particularly, a 510 first truncated prolate spherical structure having a 501 wire connector on one end and a 502 hinge connector on the other end, a 520 second truncated prolate spherical structure having a 501 wire connector on one end and a 502 hinge connector or a 503 hinge receiver on the other end, and optionally 530 one or more additional truncated prolate spherical structure having a 502 hinge connector or 503 hinge receiver on one end and having a 502 hinge connector or 503 hinge receiver on the other end while FIG. 5C illustrates one chain of 500 truncated prolate interbody implants with attached 540 one or more insertion wires, while

FIG. 7 illustrates a frontal plane view of the L5 vertebra, Sacrum and Ilium. One chain of 500 truncated prolate interbody implants with attached 540 insertion wires is positioned at the anterior region of the L5/S1 disc space. Cannulas are shown in the insertion pathway formed in the ala of the sacrum that accepts the interbody implants and wires.

FIG. 8 illustrates a frontal plane view of the Sacrum and Ilium. Two chains of 500 truncated prolate interbody implants with attached 540 insertion wires are positioned on the S1endplate. Insertion wires are shown attached to the interbody implants and in the insertion pathway formed in the ala of the sacrum.

FIGS. 10A-10I1 illustrate one embodiment of an expandable interbody implant.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

DETAILED DESCRIPTION OF INVENTION

This disclosure describes the interbody cage device and medical method for performing spinal surgical procedures in which a robot controls an instrument that creates a pathway to the spine or augmented reality is used to guide the pathway to the spine of a human by a user.

The present invention provides for an improved method for performing spinal Surgical procedures (e.g., spinal fusions) using one or more ala as the pathway L5/S1 disc space without violating the sacro-iliac joint. It should be appreciated that on each side of the body there is a continuous bony corridor from the pelvis, through the sacrum to the L5/S1 disc. Without being bound to any particular theory, these corridors can be traversed by a tunnel that would not damage or endanger any sensitive visceral or neurologic structures. The tunnels could be accessed by percutaneous incisions in the gluteal area.

The present method includes methods and techniques for positioning a patient requiring surgery in a configuration to restrict movement. Upon placement, the patient is monitored for movement in relation to one or more locations of the patients' spine. Three-dimensional (3D) imaging techniques are then used to determine the absolute position of the patients' spine and spinal features of interest to be used in conjunction with the patients' monitored movement, to allow for absolute location, in real time, of a patents spine and its features. The 3D imaging data is processed to determine the optimal pathway to the particular spinal location needing surgery for the specific patient. Using the 3D imaging data, as well as the real-time monitoring information, an end-effector of a robot is used to guide a surgical instrument to the spinal location needing surgery, or augmented reality, adjusting its pathway, in real-time, based on a patients' movement relative to the 3D imaging data. Upon creation of the pathway, the desired spinal implant is inserted into the patient. As a result of the aforementioned, the patient obtains the benefit of a spinal fusion without the potential harm created by an extensive surgical approach.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an', and "the" include singular and plural referents unless the content clearly dictates otherwise. Thus, for example, reference to "a linker" includes one or more linkers.

Unless defined otherwise, all technical and scientific terms used herein have the same meaning as commonly understood by one of ordinary skill in the art.

The phrase "ala", as used herein, generally refers to the wing-like region of the sacrum in a Subject including, but not limited to, the area of bone extending laterally from the first sacral pedicle to the ilium.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The phrase "end-effector" as used herein generally refers to an actuator or manipulator of a robotic arm that moves, directs, interacts or otherwise operates a surgical tool. In some embodiments, a surgical tool may be attached directly to the end of a mechanical or robotic arm, thus in such embodiments the surgical tool is also an end-effector.

The phrase "augmented reality" as used herein generally refers to a technology that superimposes a computer-generated image on a user's view of the real world, thus providing a composite view. A human user manipulates a surgical tool in accordance to this view. In some embodiments, a surgical tool may provide the means to access the disc space.

The phrase "sacro-spinous space" as used herein generally refers to the non-articular region dorsal to the sacral-iliac joint in a subject including, but not limited to, the area between the ilium and the dorsal sacrum.

The phrase "sacro-iliac joint" as used herein generally refers to the surface formed at the area of contact between the sacrum and the ilium.

The phrase "interbody cage" shall mean a device placed between adjacent vertebral bodies in spinal fusion surgeries to improve or enhance arthrodesis.

Beaded/Prolate Interbody Cage

At least one embodiment of the present invention provides for an interbody cage device using one or more geometric structures being capable of being delivered through surgical cannulas used in spinal surgeries through the ala or another anatomic region as the pathway to the L5/S1 disc space or any other disc space along the spine.

Figure 1:
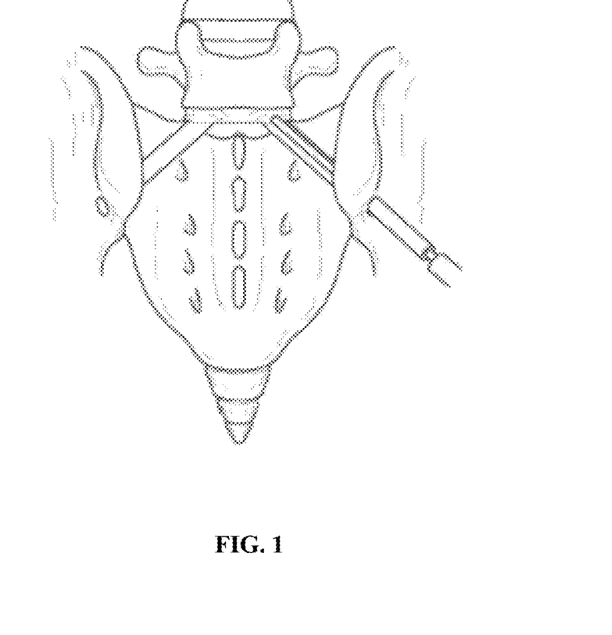
FIG. 1 provides an example of pathways formed by instruments positioned with an end-effector in the Subjects' right and left ala, L5/S1 disc and L5 vertebra.
Figure 2:
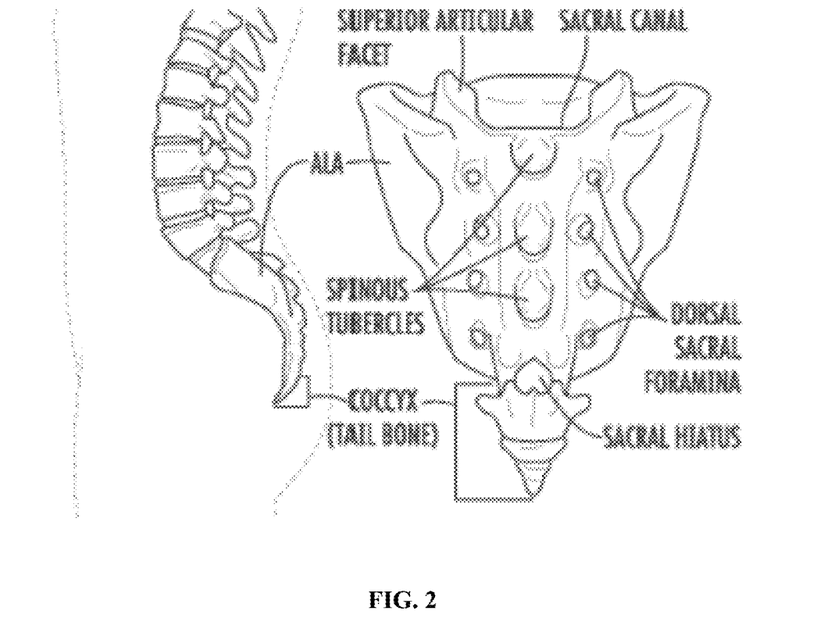
FIG. 2 describes the key anatomic structures of the sacrum.
Figure 3:
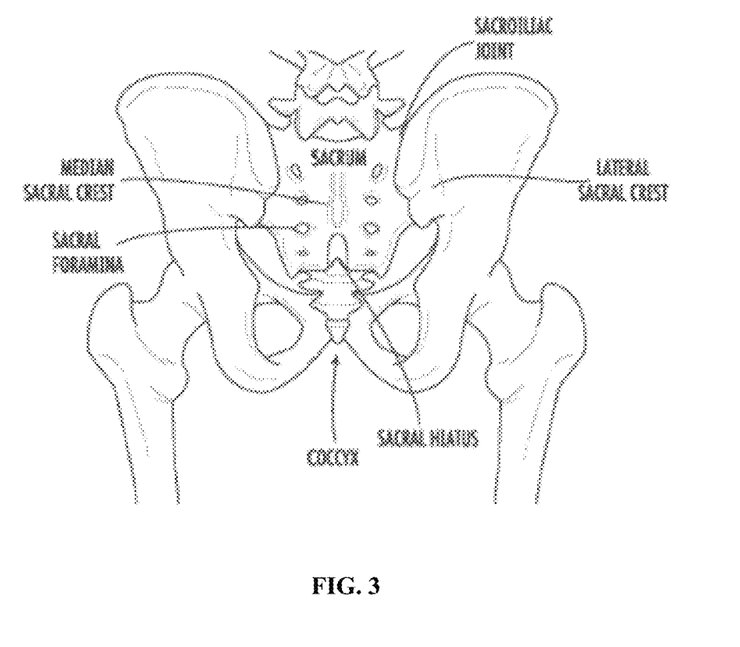
FIG. 3 describes the key anatomic structures of the sacrum and ilium.
Figure 4:
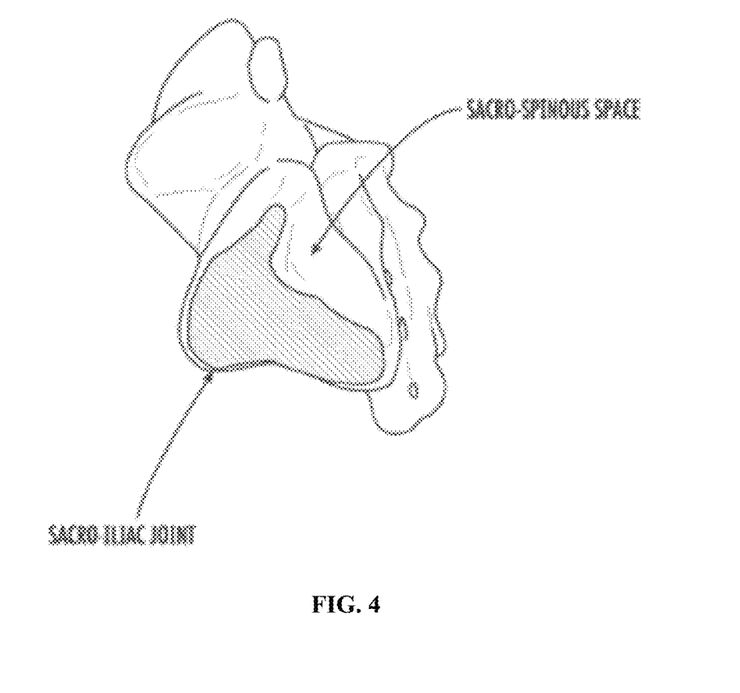
FIG. 4 describes the key anatomic structures of the sacrum.
Figure 5A:
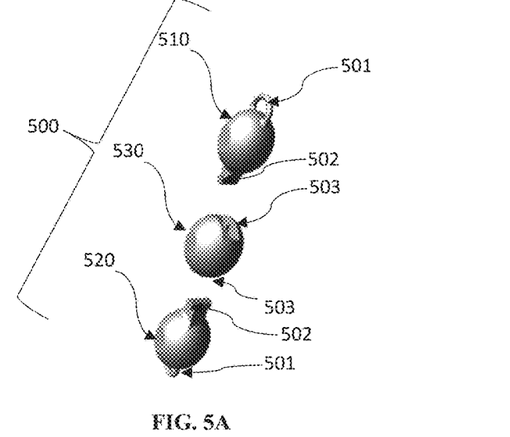
Figure 5B:
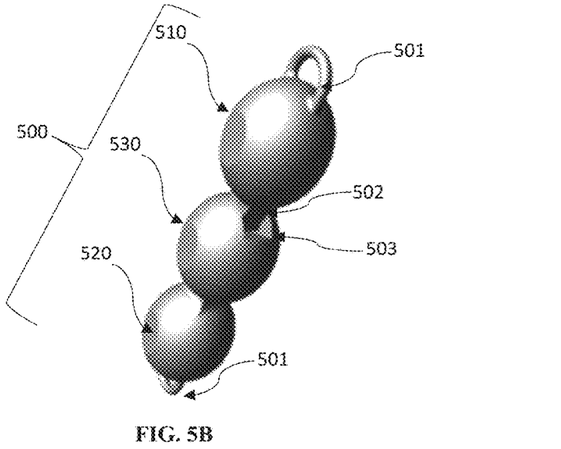
FIG. 5B illustrates the 500 prolate interbody implant interconnected illustrating the 510 first truncated prolate spherical structure interconnected with the 520 second truncated prolate spherical structure via 530 one or more additional truncated prolate spherical structure and able to articulate about the interconnections.
Figure 5C:
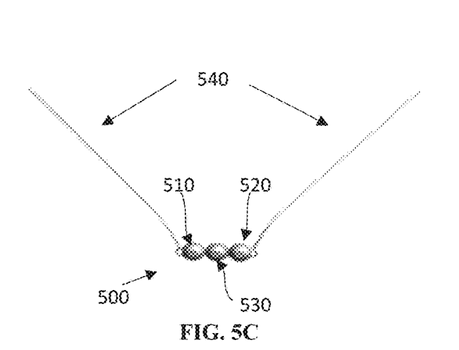
Figure 5D:
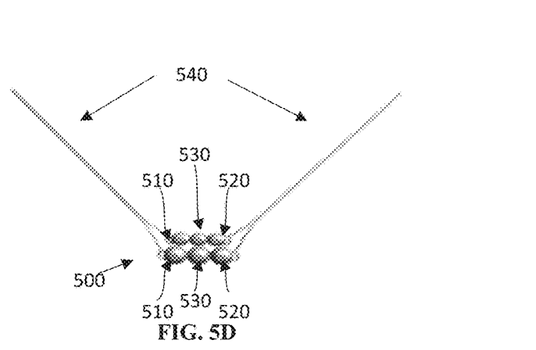
FIG. 5D illustrates two chains of the 500 truncated prolate interbody implants with attached insertion wires, FIG. 5E
Figure 5E:
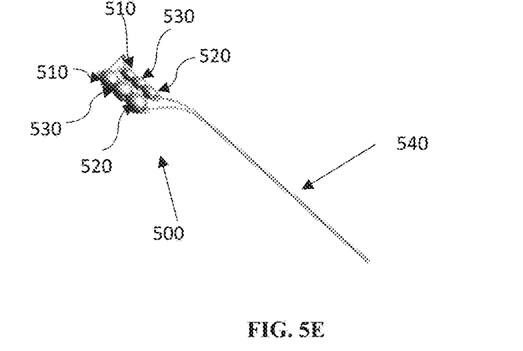
Figure 5F:
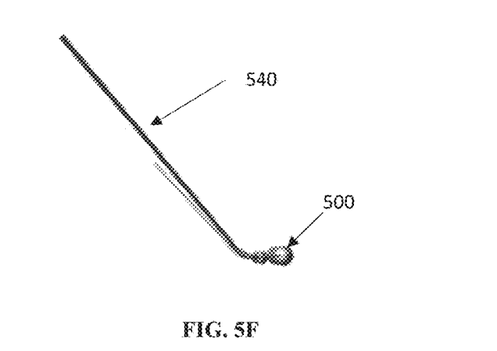
FIG. 5F illustrates different views of the two-chain 500 truncated prolate interbody implants with attached insertion wires positioned as some embodiments may require during an implant procedure.
Figure 6:
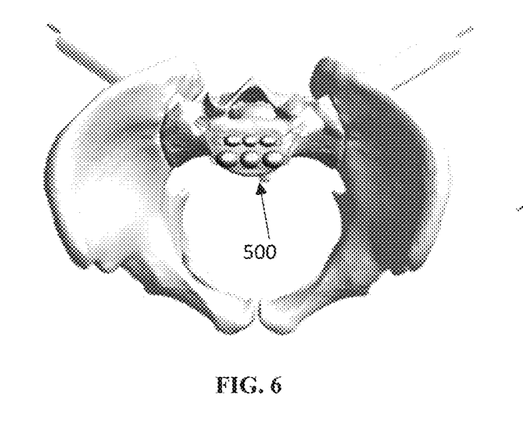
FIG. 6 illustrates a transverse plane view of the pelvis with the sacral endplate (a.k.a. S1) at the L5/S1 disc space, as illustrated, two chains of 500 truncated prolate interbody implants with attached 540 insertion wires are positioned on the S1 endplate. Anterior is to the right and posterior is to the left. The anterior chain of beads is larger in size than the posterior chain of beads to facilitate restoration of the patient's sagittal plane alignment (i.e., lordosis). Cannulas are shown in the insertion pathway formed in the ala of the sacrum that accepts the interbody implants and wires.
Figure 7:
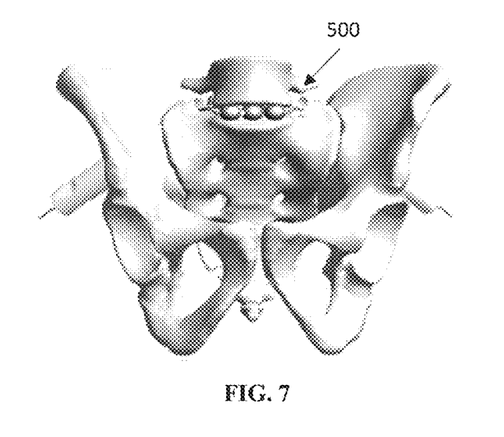
Figure 8:
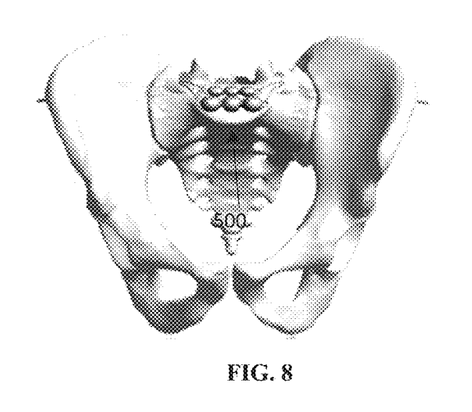
Figure 9:
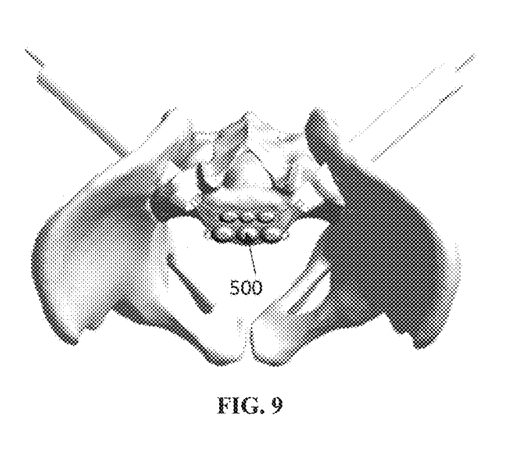
FIG. 9 illustrates identical to FIG. 7 except the pelvis is rotated in the sagittal plane to help illustrate an exemplary insertion pathway.
Figure 10A:
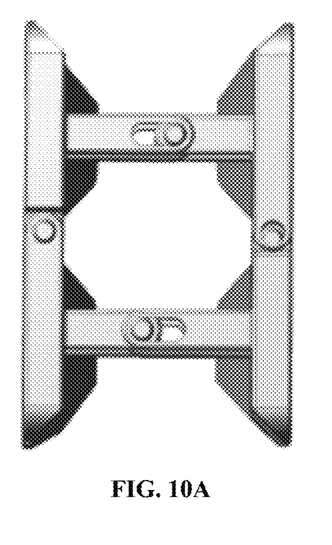
FIGS. 10A and 10B illustrate one embodiment of the expandable interbody implant., with FIG. 10A illustrating the implant in its expanded state, while FIG. 10B the implant is not expanded.
Figure 10B:
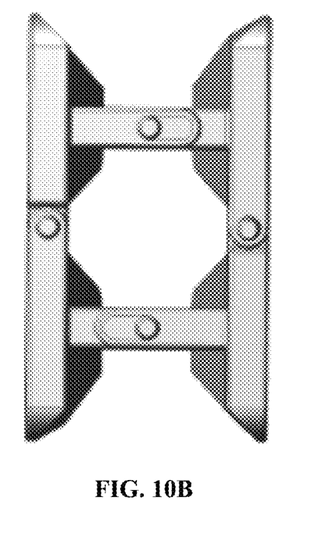
Figure 10C:
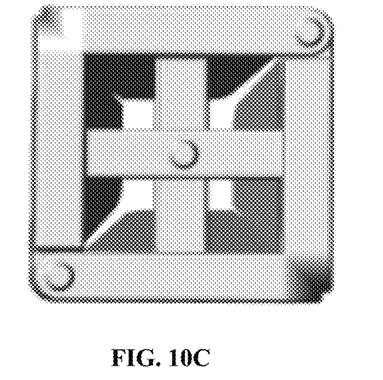
FIG. 10C and FIG. 10D illustrate different views of the expandable implant having hinged endplates to form a rectangular cuboid to allow for insertion and placement in the L5/S1 disc space.
Figure 10D:
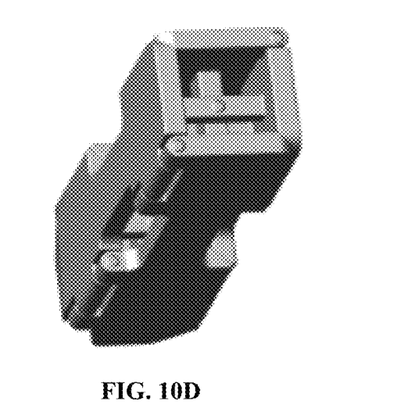
Figure 10E:
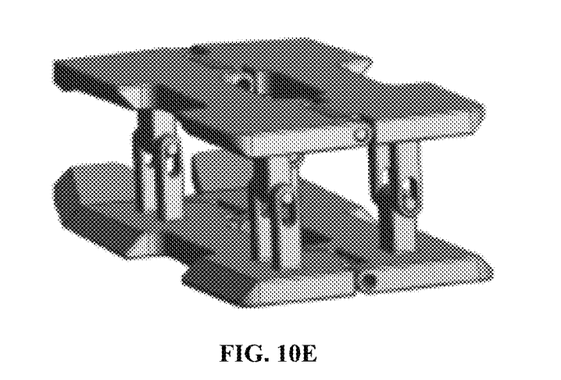
FIGS. 10E and 10F provide additional views of the the expandable interbody implant illustrating the implant in its expanded state, while FIGS. 10G and 10I1 provide additional views of the the expandable interbody implant illustrating the implant not expanded.
Figure 10F:
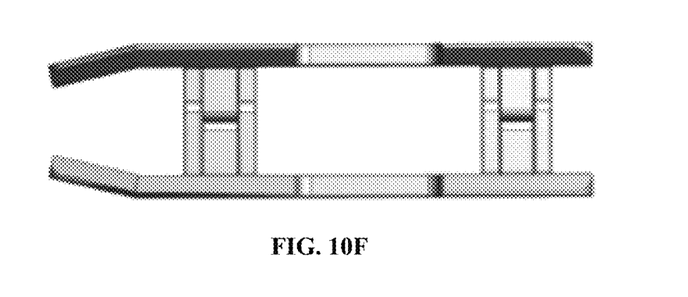
Figure 10G:
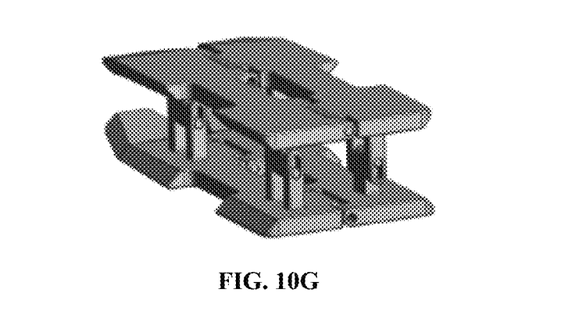
Figure 10H:
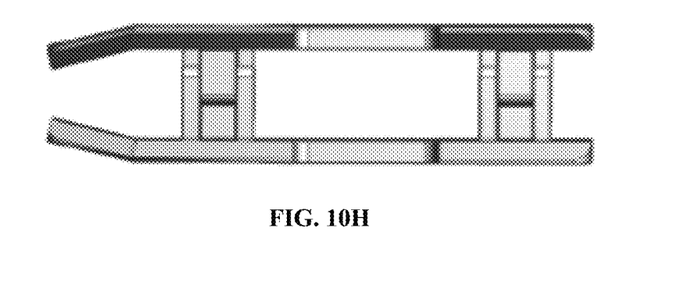
Figure 11A:
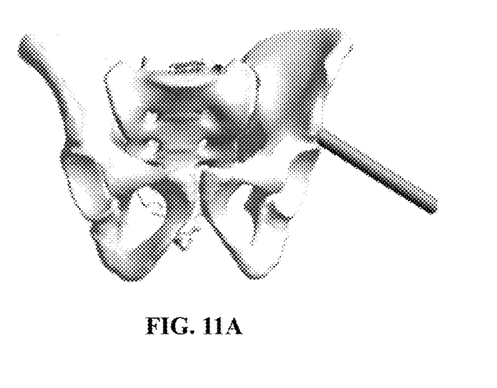
FIG. 11A illustrates a frontal plane view of the L5 vertebra, Sacrum and Ilium. The interbody implant that is depicted in FIGS. 10A-10G in its expanded state is positioned on the S1 endplate. A cannula is shown in the insertion pathway formed in the ala of the sacrum that accepts the interbody implant.
Figure 11B:
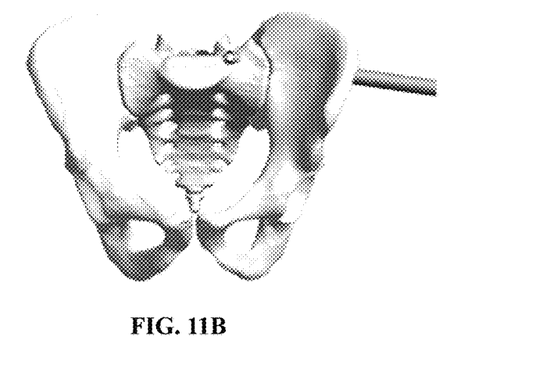
FIG. 11B illustrates a frontal plane view of the pelvis with the sacral endplate (a.k.a. S1) at the L5/S1 disc space. A cannula with a drill is shown in the insertion pathway formed in the ala of the sacrum. The drill is poised to form a shallow groove in the S1 endplate to facilitate insertion of the interbody implant.
Figure 11C:
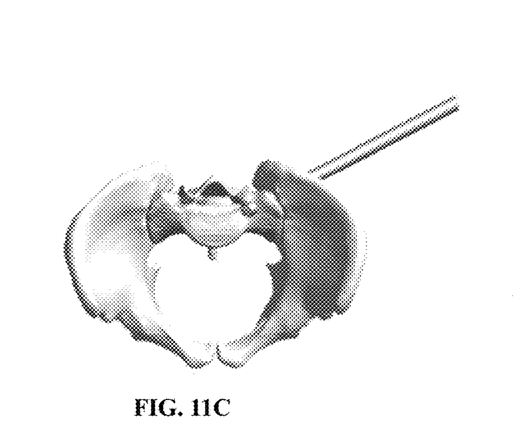
FIG. 11C illustrates a transverse plane view of the pelvis with the sacral endplate (a.k.a. S1) at the L5/S1 disc space. Anterior is to the right and posterior is to the left. A cannula with a drill is shown in the insertion pathway formed in the ala of the sacrum. The drill has formed a shallow groove in the S1 endplate to facilitate insertion of the interbody implant.
Figure 11D:
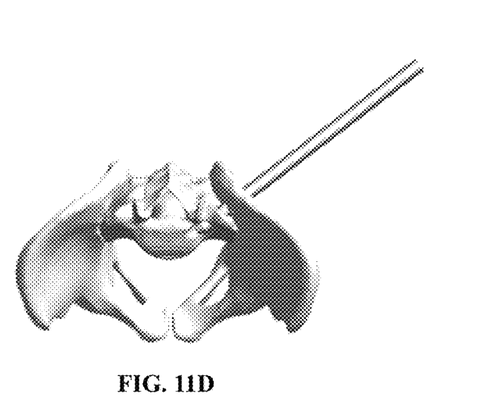
FIG. 11D is the same setup as FIG. 11B except the pelvis is rotated in the sagittal plane to help illustrate an exemplary insertion pathway.
Figure 11E:
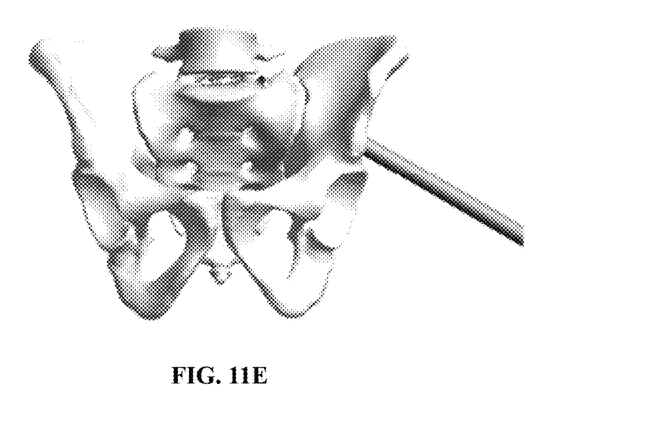
FIG. 11E illustrates a frontal plane view of the L5 vertebra, Sacrum and Ilium. The interbody implant that is depicted on FIGS. 10A-10G in its expanded state is positioned in the L5/S1 disc space. A cannula is shown in the insertion pathway formed in the ala of the sacrum that accepts the interbody implant.
Figure 11F:
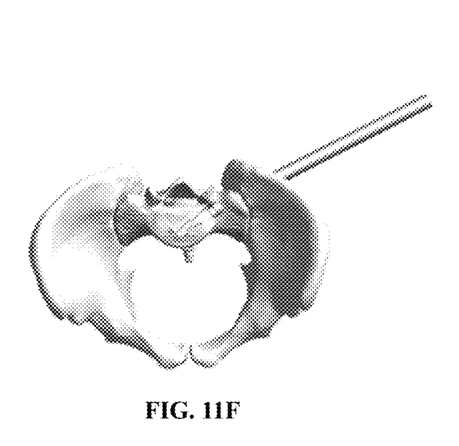
FIG. 11F illustrates a transverse plane view of the pelvis with the sacral endplate (a.k.a. S1) at the L5/S1 disc space. The interbody implant that is depicted on FIGS. 10A-10G in its expanded state is positioned on the S1 endplate. A cannula is shown in the insertion pathway formed in the ala of the sacrum that accepts the interbody implant. Anterior is to the right and posterior is to the left.
Figure 11G:
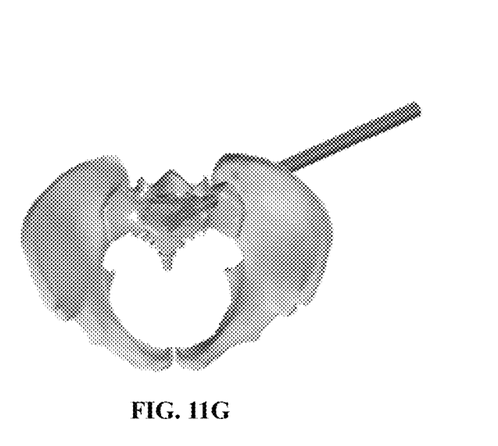
FIG. 11G illustrates almost the same as FIG. 11B except the interbody implant is positioned slightly out of alignment with the insertion pathway. This is a potential repositioning that the surgeon might execute after the initial insertion in order to position the implant in the most favorable location of the disc space to restore height between the adjacent vertebrae.
Figure 12A:
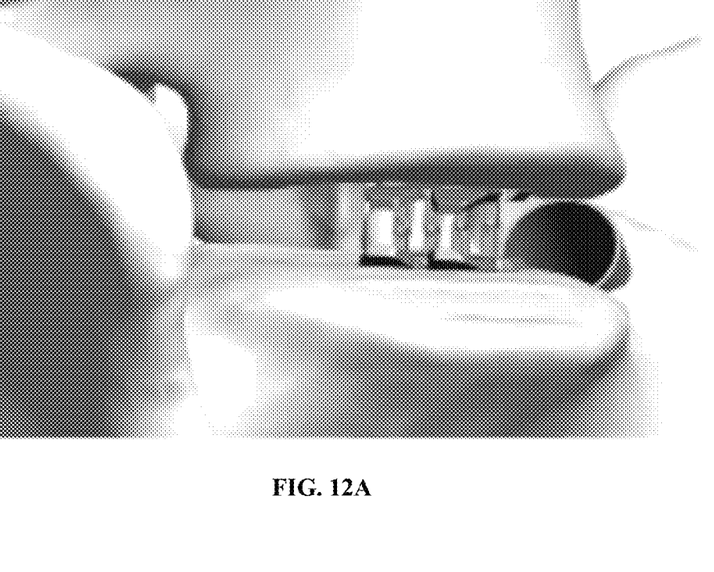
FIGS. 12A and 12B illustrate one embodiment of the expandable interbody implant after iplant., with FIG. 12A illustrating the implant in its expanded state, while FIG. 12B the implant is not expanded.
Figure 12B:
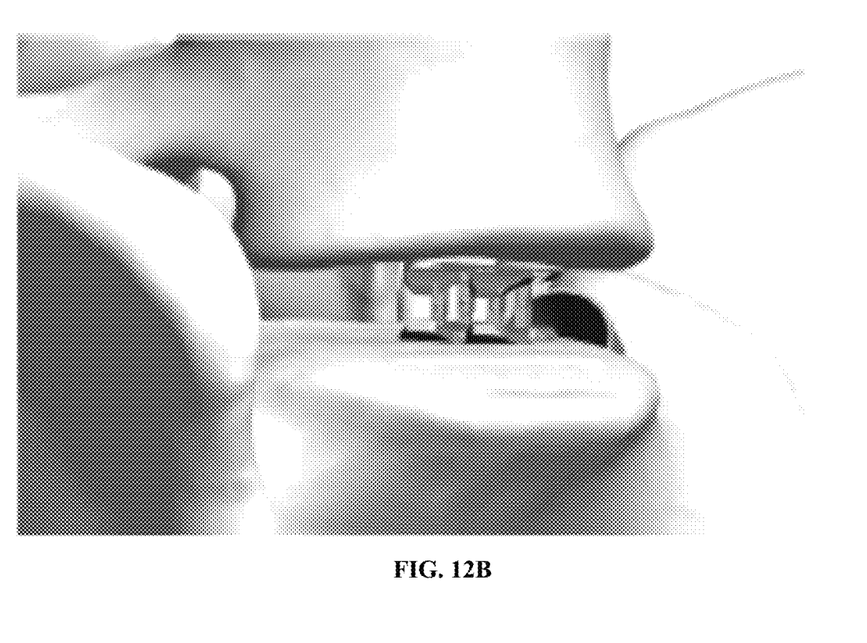

Without intending to limit the geometric structure which may be used, in at least one embodiment the geometric shape of the interbody cage device is a truncated prolate sphere. FIGS. 5A-5F illustrate different embodiments where the geometric structure is a truncated prolate sphere. In such embodiments the interbody cage device includes a first truncated prolate spherical structure having a diameter capable of being inserted through a cannula inserted in the ala or another anatomic region as the pathway to the L5/S1 disc space or any other disc space along the spine and at least a second truncated prolate spherical structure, having the same or similar diameter of said first spherical structure. In such embodiments, the spherical structures are connected to each other in such a way that allows for each truncated prolate spherical structure to articulate independently within at least one plane of motion relative to each other. Without being bound to a particular theory, it is believed that such embodiment enables the interbody cage device to be delivered via a cannula with the ability for passing around a corner to be inserted through a cannula through the ala or another anatomic region to the L5/S1 disc space or any other disc space along the spine. Use of such interbody cage device enables quick and easy placement of the interbody in a controlled manner while also providing a robust means for implant fixation to the bone.

In at least one embodiment, the geometric structures making up the interbody cage device use a connection means allowing for the connection, yet independent articulation of, one geometric structure to another. In at least one embodiment, the connection means is one or more eyelets on the leading and/or trailing geometric structure that enable the assembly to be positioned in the disc space. In another embodiment the leading and/or trailing geometric structure enables the assembly to be affixed to the sacrum. Without being bound to a particular theory, it is believed that linking multiple beads increases the cage's structural strength to withstand applied in vivo loading while providing for graft containment. In at least one embodiment, a plurality of truncated prolate spherical structures connected to articulate within at least one plane of motion relative to each said plurality of truncated prolate spherical structures are used.

Insertion of the interbody cage devices using independent geometric structures may be accomplished using at least one surgical wire attached to one end of the interbody cage device, and at least one wire attached to the other end of the interbody cage device. In such embodiments, the surgical wire is inserted to the L5/S1 disc space through at least one cannula, then through a second cannula, allowing for the interbody cage device to be moved through said first cannula and placed in the L5/S1 disc space through a force applied to one or more ends of the interbody cage device through the wires, where the independent articulation of the cage elements allow for the movement of the cage device around corners. It should be understood that, to optimally place such interbody cage devices, movement of the interbody cage device through the use of the wires allows for the prolate spherical structures to articulate independent to each other for placement in the L5/S1 disc space through the ala.

Expandable Interbody Cage

At least one embodiment of the present invention provides for an interbody cage device capable of being inserted through the ala as the pathway to the L5/S1 disc space, using at least two or more endplates having a width capable of being inserted through a cannula inserted in the ala as the pathway to the L5/S1 disc space, and at least one hinge between the two or more endplates. Once said interbody cage device is inserted through a cannula to the L5/S1 disc space the two or more endplates are capable of being extended about the hinge. In at least one embodiment, two or more endplates are at least four endplates to form a rectangular cuboid when placed in the L5/S1 disc space.

Without being bound to a particular theory it is believed that by utilizing folding endplates, the folded endplates reduce the footprint during its delivery to the disc space. This allows the interbody to be delivered via a cannula which is a more minimally invasive corridor (i.e., portal) than what is typical today.

In at least one embodiment, the at least one hinge between the end plates is a plurality of hinges. It is believed that use of such plurality of hinges, instead of a unitary hinge, enables the inventive cage device to be deployed around a corner. Use of these features allow for quick and easy placement of the interbody, particularly when using minimally invasive approaches through the ala to the L5/S1 disc space.

In at least one embodiment, the at least one hinge between the end plates provides a means to expand the cage in one or more directions. Use of these features allows for the desired spacing between two vertebrae.

In at least one embodiment, the at least one hinge between the end plates provides a means to angle the end plates of the cage in one or more directions. Use of these features allows for the desired angulation between two vertebrae.

Robot and Augmented Reality Techniques

A type of minimally invasive surgery is provided which currently involves using a robot to access internal cavities, bones and organs within Subjects. Robotic surgery has been used in spinal surgeries, for example, to provide accurate placement of pedicle screws. Robotic surgery provides benefits in that the accuracy in positioning the screw within the pedicle reduces the incidence of bony perforation, and thus provides a reduced risk of nerve injury to the Subject. A further practical consequence and advantage of using robotic spine surgery is that surgeons experience less exposure of ionizing radiation because less or no fluoroscopy is necessary to perform the actual procedure.

A type of minimally invasive surgery is provided which currently involves using a augmented reality to access internal cavities, bones and organs within Subjects. Augmented reality surgery has been used in spinal surgeries, for example, to provide accurate placement of pedicle screws. Augmented reality surgery provides benefits in that the accuracy in positioning the screw within the pedicle reduces the incidence of bony perforation, and thus provides a reduced risk of nerve injury to the Subject. A further practical consequence and advantage of using augmented reality spine surgery is that surgeons experience less exposure of ionizing radiation because less or no fluoroscopy is necessary to perform the actual procedure.

With use of robotic techniques, positioning a portion of at least one surgical instrument with an end-effector is advantageous because of the accuracy afforded by the robot. In some embodiments, a method may at least include positioning a portion of at least one surgical instrument with an end-effector in at least one ala to enable all or a portion of a surgical procedure to be performed.

In some embodiments, a method may at least include positioning a portion of at least one surgical instrument with an end-effector through at least one ala and sacro-spinous space to enable all or a portion of a surgical procedure at the L5/S1 disc space to be performed.

In some embodiments, a method may at least include positioning a portion of at least one surgical instrument with an end-effector through at least one ala to enable all or a portion of a surgical procedure at the L5/S1 disc space and the L5 vertebra to be performed.

In some embodiments, a method may at least include positioning a portion of at least one surgical instrument with an end-effector through at least one ala to enable all or a portion of a surgical procedure at the ala, L5/S1 disc space and the L5 vertebra to be performed.

In some embodiments, a method may at least include positioning a portion of at least one surgical instrument with an end-effector through at least one ala to enable all or a portion of a surgical procedure at one or more of the ala, L5/S1 disc space and the L5 vertebra to be performed.

In some embodiments, a method may at least include positioning a portion of at least one surgical instrument with an end-effector through at least one ala to enable all or a portion of a surgical procedure at one or more of the ala, L5/S1 disc space and the L5 vertebra to be performed and a non-robotic method for positioning at least one implant in one or more of the: L5 vertebra, L5/S1 disc space and the sacrum.

In some embodiments, a method may at least include a portion of at least one surgical instrument positioned with an end-effector, a controller for controlling the position of the end-effector and a measurement system with a computer processor for measuring: by the processor, a position of the ala of the patient; determining by the processor a change in the position of the ala; and automatically adjusting, via the robot, the position of the end-effector based at least in part on a change in the position of the ala; and automatically adjusting, via the robot, the position of the end-effector to create a pathway in the ala.

In some embodiments, a method may at least include a portion of at least one surgical instrument positioned with an end-effector, a controller for controlling the position of the end-effector and a measurement system with a computer processor for measuring: by the processor, a position of the ala and L5 vertebra of the patient; determining by the processor a change in the position of the ala and L5 vertebra; and automatically adjusting, via the robot, the position of the end-effector based at least in part on a change in the position of the ala and L5 vertebra; and automatically adjusting, via the robot, the position of the end-effector to create a pathway in the ala and L5 vertebra.

In some embodiments, a method may at least include positioning a portion of at least one surgical instrument with an end-effector so that at least one ala and the L5 vertebra are oriented to enable all or a portion of at least one surgical instrument to be positioned.

In some embodiments, a method may at least include positioning a portion of at least one surgical instrument with an end-effector so that at least one ala and the L5 vertebra are oriented to enable all or a portion of at least one surgical implant to be positioned.

In some embodiments, a method may at least include positioning a portion of at least one surgical instrument with an end-effector so that at least one ala and the L5 vertebra are oriented to enable all or a portion of at least one surgical instrument and surgical implant to be positioned.

In some embodiments, a method may at least include a portion of at least one surgical instrument positioned with an end-effector, a controller for controlling the applied load by the end-effector and a measurement system with a computer processor for measuring: by the processor, a displacement of the end-effector.

In some embodiments, a method may at least include a portion of at least one surgical instrument positioned with an end-effector, a controller for controlling the applied load by the end-effector and a measurement system with a computer processor for measuring by the processor, a displacement of the end-effector after contacting at least one of the ala and L5 vertebra of the patient.

With use of augmented reality techniques, positioning a portion of at least one surgical instrument by the surgeon is advantageous because of the accuracy afforded by the augmented reality software and user interface. In some embodiments, a method may at least include positioning a portion of at least one surgical instrument in at least one ala to enable all or a portion of a surgical procedure to be performed.

In at least one embodiment, the implant used in such techniques includes an interbody cage device using at least one geometric shape, including those as described herein, or an expandable interbody cage device, including those as described herein.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. An interbody cage device comprising:
a first truncated prolate spherical structure having a diameter capable of being inserted through a pathway to a disc space and further having at least one wire connector on a first end and a hinge connector or a receiver for a hinge connector on a second end, wherein said at least one wire connector is a loop, and wherein said first truncated prolate spherical structure is independently articulatable;
a second truncated prolate spherical structure being hingedly connected to said first truncated prolate spherical structure and further having at least one wire connector on a first end and a hinge connector or a receiver for a hinge connector on a second end for connecting to said first truncated prolate spherical structure, wherein said second truncated prolate spherical structure is independently articulatable; and
at least one surgical wire being connected to said at least one wire connector of said first truncated prolate spherical structure;
wherein said at least one surgical wire is adapted to adjust a position of one or more of said first truncated prolate spherical structure and said second truncated prolate spherical structure within the disc space by external manipulation.

2. The interbody cage device of claim 1, further comprising an additional plurality of truncated prolate spherical structures each connected to articulate within at least one plane of motion relative to another of said additional plurality of truncated prolate spherical structures, wherein said one end of each additional plurality of truncated prolate spherical structures has a hinge connector or a receiver for a hinge connector on one end and a hinge connector or a receiver for a hinge connector on a second end.

3. The interbody cage device of claim 1, wherein the pathway to said disc space is through the ala.

4. The interbody cage device of claim 1, wherein said disc space is L5/S1.

5. The interbody cage device of claim 2, wherein at least one of said first truncated prolate spherical structure, said second truncated prolate spherical structure, or said additional plurality of truncated prolate spherical structures has a diameter capable of being inserted through a cannula inserted in the ala as the pathway to said disc space.

6. The interbody cage device of claim 1, wherein said interbody cage device is composed of synthetic or biologic biocompatible materials of titanium, stainless steel, polyether ether ketone (PEEK), Polyaryletherketone (PAEK), bone autografts, allografts, synthetic biological materials, synthetic bone graft substitute materials, or combinations thereof.

7. An interbody cage device comprising:
a first truncated prolate spherical structure having a diameter capable of being inserted through a pathway to a disc space, said first truncated prolate spherical structure having at least one wire connector on a first end and a hinge connector or a receiver for a hinge connector on a second end, wherein said at least one wire connector is a loop, and wherein said first truncated prolate spherical structure is independently articulatable;
a second truncated prolate spherical structure, said second truncated prolate spherical structure having at least one wire connector on a first end and a hinge connector or a receiver for a hinge connector on a second end for connecting to said hinge connector of said first truncated prolate spherical structure, wherein said at least one wire connector is a loop, and wherein said second truncated prolate spherical structure is independently articulatable;
a third truncated prolate spherical structure being hingedly connected to said first truncated prolate spherical structure via said second truncated prolate spherical structure, said third truncated prolate spherical structure having a hinge connector or a receiver for a hinge connector on a first end and a hinge connector or a receiver for a hinge connector on a second end, wherein said third truncated prolate spherical structure is independently articulatable;
wherein said connection of said second truncated prolate spherical structure to said first truncated prolate spherical structure and said connection of said second truncated prolate spherical structure to said third truncated prolate spherical structure allows for said second truncated prolate spherical structure to articulate within at least one plane of motion relative to said first and third truncated prolate spherical structures; and at least one surgical wire adapted to adjust a position of one or more of said first truncated prolate spherical structure, said second truncated prolate spherical structure, and said third truncated prolate spherical structure within the disc space by external manipulation.

8. The interbody cage device of claim 7, wherein the pathway to said disc space is through the ala.

9. The interbody cage device of claim 7, wherein said disc space is L5/S1.

10. The interbody cage device of claim 7, wherein at least one of said first truncated prolate spherical structure, said second truncated prolate spherical structure, or said third truncated prolate spherical structure has a diameter capable of being inserted through a cannula inserted in the ala as the pathway to said disc space.

11. The interbody cage device of claim 7, wherein said interbody cage device is composed of synthetic or biologic biocompatible materials of titanium, stainless steel, polyether ether ketone (PEEK), Polyaryletherketone (PAEK), bone autografts, allografts, synthetic biological materials, synthetic bone graft substitute materials, or combinations thereof.

12. An interbody cage device comprising:
a plurality of truncated prolate spherical structures each having a diameter capable of being inserted through a pathway to a disc space, and further having at least one wire connector on a first end and a hinge connector or a receiver for a hinge connector on a second end, wherein said at least one wire connector is a loop, and wherein each truncated prolate spherical structure is independently articulatable and hingedly connected to another truncated prolate spherical structure of said plurality of truncated prolate spherical structures; and
at least one surgical wire being connected to said at least one wire connector of at least one of said plurality of truncated prolate spherical structures;
wherein the at least one surgical wire is adapted to adjust a position of said plurality of truncated prolate spherical structures within the disc space by external manipulation.

13. The interbody cage device of claim 12, further comprising an additional plurality of truncated prolate spherical structures each having a hinge connector or a receiver for a hinge connector on a first end and a hinge connector or a receiver for a hinge connector on a second end, and each hingedly connected to articulate within at least one plane of motion relative to another of said additional plurality of truncated prolate spherical structures.

14. The interbody cage device of claim 12, wherein the pathway to said disc space is through the ala.

15. The interbody cage device of claim 12, wherein said disc space is L5/S1.

16. The interbody cage device of claim 12, wherein each truncated prolate spherical structure has a diameter capable of being inserted through a cannula inserted in the pathway to said disc space.

17. The interbody cage device of claim 12, wherein said interbody cage device is composed of synthetic or biologic biocompatible materials of titanium, stainless steel, polyether ether ketone (PEEK), Polyaryletherketone (PAEK), bone autografts, allografts, synthetic biological materials, synthetic bone graft substitute materials, or combinations thereof.

18. A method of insertion of an interbody cage device, the method comprising:
providing the interbody cage device of claim 1;
inserting said at least one surgical wire through at least one pathway, allowing for said interbody cage device to be placed in a disc space through force applied to said first truncated prolate spherical structure through said at least one surgical wire; and
adjusting the position of the interbody cage device through external manipulation of said at least one surgical wire.

19. The method of insertion of claim 18, wherein said placing of the interbody cage device through the use of said at least one surgical wire allows the interbody cage device to be placed in the L5/S1 disc space through said at least one pathway.

20. The method of insertion of claim 19, wherein said at least one pathway is the ala.

21. The method of insertion of the interbody cage device of claim 18, wherein said at least one surgical wire comprises a first surgical wire and a second surgical wire, wherein said first surgical wire is attached to said at least one wire connector on said first truncated prolate spherical structure, and said second surgical wire is attached to said at least one wire connector on said second truncated prolate spherical structure; and wherein said first surgical wire is inserted through said at least one pathway, allowing for said interbody cage device to be placed in said disc space through force applied to said interbody cage device through said first surgical wire or said second surgical wire.

* * * * *